United States Patent

Wood et al.

[11] 4,301,675
[45] Nov. 24, 1981

[54] MEASUREMENT OF HIGH CONSISTENCY

[75] Inventors: John R. Wood, Dorion; Joseph B. S. Beaulieu, Pointe Claire, both of Canada

[73] Assignee: Domtar Inc., Montreal, Canada

[21] Appl. No.: 120,151

[22] Filed: Feb. 11, 1980

[51] Int. Cl.³ .................. G01N 11/08; G01N 33/34
[52] U.S. Cl. ............................................ 73/56; 73/63
[58] Field of Search ................ 73/63, 61 R, 56; 162/198, 258, 263

[56] References Cited

U.S. PATENT DOCUMENTS

| | | | |
|---|---|---|---|
| 1,826,732 | 10/1931 | Chatillon | 73/56 |
| 2,076,592 | 4/1937 | Rhodes | 73/56 |
| 3,271,999 | 9/1966 | Dwyer et al. | 73/61 R |
| 3,718,030 | 2/1973 | Kesler | 73/61 R |

*Primary Examiner*—Gerald Goldberg
*Assistant Examiner*—Joseph W. Roskos

[57] ABSTRACT

A method and apparatus for determining the consistency of pulps by squeezing the pulp in a press and registering the pressure required to initiate the flow of water from said pulp, said pressure being indicative of the consistency of the sample.

8 Claims, 2 Drawing Figures

MEASUREMENT OF HIGH CONSISTENCY

FIELD OF THE INVENTION

The present invention relates to a method of determining the consistency of a high consistency pulp. More specifically, the present invention relates to rapid method of determining high consistency of pulp in the range of 15-55% by a pressing operation.

BACKGROUND TO THE INVENTION

The measurement of consistency is an important operation of any mechanical pulp, yet no reasonably reliable, relatively quick test an available for determining consistency of pulp of higher consistencies.

In a mechanical pulp mill, pulp is produced by working (refining) wood chips or the like between a pair of opposed plates in a conventional disc type refiner. This pulping operation is carried out at a relatively high pulp consistency (generally in the range of 25-50%). Obviously it is important that the plates, which are biased toward one another by the pressure load on the refiner during operation not clash as this will damage them. There are three main variables which effect the plate spacing namely, the setting of disc spacing, the specific energy applied to the pulp, and the consistency of the pulp. Generally the discs are first set at a zero spacing where the plates do not clash under no load conditions. The load is applied by feeding pulp between the discs. This load actually deflects the discs and moves them farther apart towards their peripheries which permits the disc setting to be reduced, i.e. the discs moved closer together so that the discs spacing at full load operation would result in the discs clashing together if there were no pulp between the discs. The refiners are generally operated at full motor load for a pre-set feed rate and to obtain a targeted specific energy application to the pulp. To apply the targeted specific energy the disc spacing is set as required. The consistency of this pulp has a significant effect on the pressure between the plates, i.e. the forces tending to hold the plates apart. If the consistency is reduced significantly the pressure between the plates will reduce and may cause the discs to clash and damage the refiner. It is thus a major advantage to know the consistency of pulp leaving the refiner, but there is no adequate means for measuring the moisture content of the wood entering the system or the amount of moisture flashed in the refiner and leaving the system as steam both of which contribute significantly to consistency. Thus no reliable method of measuring the in-coming wood is available that will give a clear indication of consistency.

It is well known to measure the consistency of the pulp leaving the refiner however such measurement cannot be accomplished rapidly and provide reliable results at the consistencies normally found in refining.

One of the standard methods of measuring consistency currently used in mills requires obtaining a sample, weighing the sample, driving off the moisture, and weighing the residual to obtain a ratio of liquid to bone-dry solids in the pulp. Such a procedure obviously is time consuming. Modified versions are used in the mills, but due to the elaborate procedures and normal mill working environments, such procedures have been found to be relatively inaccurate.

An experienced operator can estimate quite accurately the consistency of a pulp sample in the range of 15-50% by sensing from the pressure his hand must exert to squeeze out water therefrom. However, such judgement is obviously subjective and can only be developed by long experience in the mill and thus is not a satisfactory control test for mill operation unless the operator has had the necessary experience.

Consistency measurement of chemical pulp of high consistency is not as prevelent as with mechanical pulps but there are applications where such measurement is required.

BRIEF DESCRIPTION OF THE INVENTION

It is the object of the present invention to provide a consistency meter that is easy to operate and provides reasonably accurate results to facilitate mill control.

The present invention relates to a method and apparatus for determining the consistency of a pulp comprising placing a sample of pulp at a consistency of between about 15 and 55% into a container, supporting said sample of pulp on a foraminous support means to permit passage of water from said pulp through said foraminous means, a water outlet from said container, pressing means pressing the pulp in the container against the foraminous support to squeeze water therefrom, and means to senses the pressure required to initiate a flow of water through said outlet, said pressure being indicative of the consistency of the pulp sample.

BRIEF DESCRIPTION OF THE DRAWINGS

Further features, objects and advantages will be evident from the following detailed description of the preferred embodiments of the present invention, taken in conjunction with the accompanying drawings in which.

DESCRIPTION OF THE PREFERRED EMBODIMENTS

Figure 1:
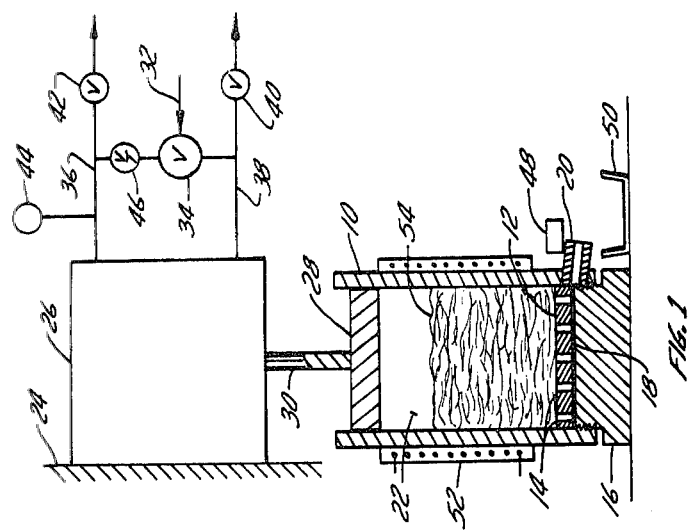
FIG. 1 is the partial section schematically illustrating the present invention.

As shown in FIG. 1 the apparatus of the present invention generally comprises a pressure chamber or container 10 having a foraminous plate 12 with perforations 14 therein forming the bottom thereof. The plate 12 is supported on a suitable removable plug 16 which as indicated is threadably received in the bottom of the container 10 and provides a liquid passage 18 between the bottom of the plate 12 and a liquid outlet 20. The container 10 forms an open ended upper chamber 22 and mounted above the chamber on a suitable support 24 is, in the illustrated arrangement, a pneumatic cylinder 26 having a piston 28 which projects into and cooperates with the open chamber 22 in the manner of a piston and cyclinder arrangement. The piston 28 is connected to the pneumatic cyclinder 26 by a piston rod 30.

The pneumatic cyclinder 26 is activated via air pressure entering from line 32 to valve 34 which directs the air selectively to lines 36 or 38. Line 36 applies pressure to the piston 28 to force it downward in the chamber 22 toward the foraminous plate 12 and line 38 applies air pressure to retract the piston 28. Obviously when line 36 is connected to the pressure in line 32 the valve 42 will be closed and valve 40 in line 38 open to permit exhaust of the opposite side of the piston in the pneumatic cyclinder 26 and similarly when air is connected to line 38 the valve 40 is closed and valve 42 will be open.

Line 36 is provided with a suitable pressure gauge 44 to indicate the air pressure in the cyclinder 26 as the piston 28 is being lowered. The rate of descent of the piston 28 or more specifically the rate of increase in pressure applied by the piston 28 to the pulp sample is controlled. This may be accomplished for example by connecting the line 32 to the line 36 via a throttling valve generally indicated at 46, preferably the air pressure will be applied to initially advance the piston 28 relatively quickly until it is about to contact the pulp sample and then at a slow controlled substantially uniform rate as it compresses the sample contained within the chamber 22. Preferably the rate of increase in pressure during compression of the pulp will be at about 4 psi per second. This rate is not critical. However, if the pressure is increased too slowly it will simply increase the time required to complete the test if the pressure is increased too quickly it may act as an impact and distort the results. Generally this rate of increase should not exceed about 40 psi per second nor will it normally be less than 1 psi per second.

As above indicated a pulp sample is placed within the chamber 22 and squeezed by a gradual increase in pressure applied via the piston 28 to initiate the flow of water through the plate 12 and out the outlet 20. This flow of water may be visually detected, i.e. manually, and a valve 46 and/or 34 closed off and the pressure reading on the gauge 44 obtained or alternatively a suitable automatic detector 48 may be provided to automatically also operate the valve 46 or signal a sensor to register the pressure on gauge 44 the instant water is sensed.

Suitable means such as the tray 50 may be provided to catch liquid expelled through the outlet 20.

It has been found that the temperature of the sample being tested should be at some selected value and for this reason it is preferred to surround the cylinder 10 with a suitable electric heater as schematically indicated at 52 which holds the temperature of the sample substantially constant at a preset temperature between 20°-99° C. preferably at 70° C.

In operation a pulp sample generally indicated at 54 is placed within the open ended chamber 22 with the piston 28 retracted and with the foraminous plate 12 fixed in position by the plug 16. The piston 28 is then lowered into the open ended chamber 22 by pressure is applied from line 32 via valve 46 and line 36 to drive the piston 28 against the top of the sample 54. After the piston 28 reaches this position pressure is increased more slowly and at a substantially uniform rate by controlling the flow through valve 46 and to advance piston 28 until a flow of water through the outlet spout 20 is initiated. At this point the pressure in the cylinder 26 is registered via a gauge 44. It has been found that there is an accurate correlation between this pressure and the consistency of the pulp sample. Advantageously the size of the sample need not be measured it is only necessary to place a reasonable size sample within the chamber 22 and to apply the pressure. By a reasonable size sample it will be apparent it must be large enough to cover the bottom 12 and sufficiently large that the water squeezed from the sample which designates the pressure and thus the consistency of the pulp sample (generally about 1 cc) does not constitute a significant portion of the water in the sample, i.e. the sample will normally be greater than about 25 gm and will not over-fill the chamber 22. Obviously when the test is completed the valves 34, 40 and 42 are adjusted to direct air via line 38 to lift the piston 28 out of the chamber 10. The chamber 10 is then separated from the plug 16 and foraminous bottom 12 to facilitate withdrawl of the squeezed pulp sample 24. The apparatus may then be reassembled and another test begun. The duration of such test is relatively short, the full test may be completed in approximately one minute.

Maximum pressure applied to the pulp is generally in the order of 240 to 325 pounds per square inch gauge. To facilitate operation using conventional air pressure in the mill, the size of the piston and cylinder arrangement 26 should be approximately four times that of the piston 28 (assuming conventional 80 psi air in the mill). However, if a simple mechanical pressure device is used or alternatively hydraulic pressure is used or if higher pressure air is available the arrangement can be adjusted to any suitable means providing the pressure in the range of, say, 200-350 psig on the pulp.

Figure 2:
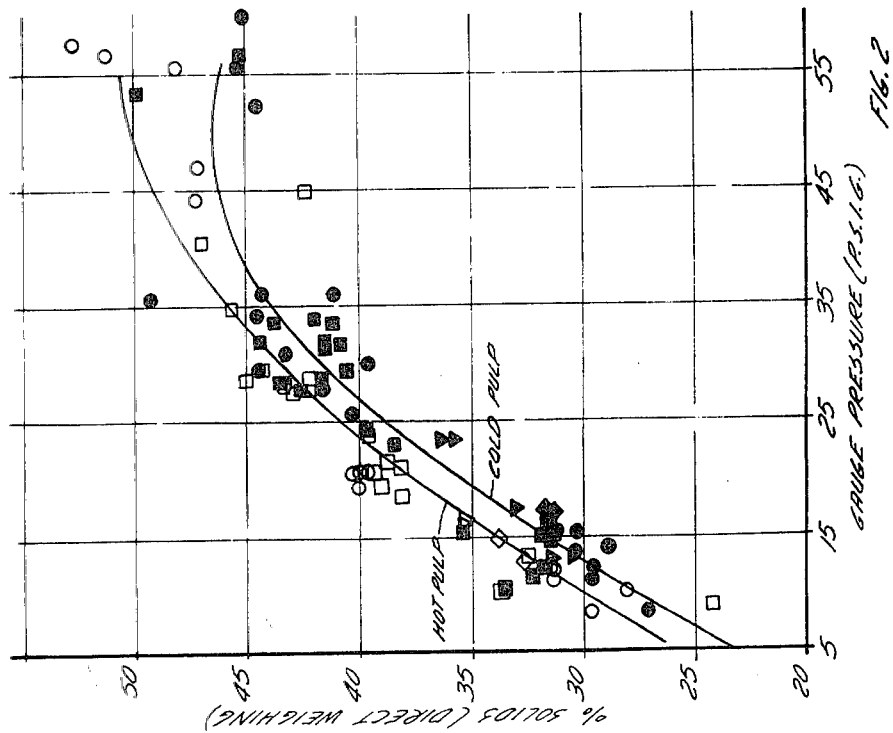
FIG. 2 is a plot of pressure vs consistency in percent solids illustrating the operation of the present invention on mechanical pulps.

FIG. 2 is a plot of the results obtained from numerous tests performed on a variety of different mechanical pulps and shows a comparison of pressure registered by gauge 44 with the actual consistency of the pulp. Some 90 runs were made (not all reported in FIG. 2) on mechanical pulps varying in consistency from 20 to 55%, with freeness ranging between 636 to 110 millimeters and at temperatures between 70 degrees and 20 degrees C. Results plotted in FIG. 2 show the correlation of pressure with consistency with the upper curve depicting operation on the hot pulp (approximately 60° C.) and the lower curve tests applied to colder pulps (approximately 30° C.).

The points plotted in FIG. 2 are differentiated as follows, the closed symbols are at low temperature (30° C.) and the open symbols at high temperature (60° C.) and the rate of pressure rise was 4 psi per second.

The various points in FIG. 2 represent the following.

| Designation | Sample Origin | Freeness C.S.F. |
| --- | --- | --- |
| • | Chip Refiner | 175-320 |
| • | Chip Refiner | 175-320 |
| ☐ | Chip Refiner | 110-174 |
| ♭ | Chip Refiner | 110-174 |
| △ | Press Master | 636 |
| ▽ | Reject Refiner | — |
| ▼ | Reject Refiner | — |

It can be seen that there is a very good correlation between the percent solids (consistency) obtained by the direct measurement technique which is relatively accurate indication of consistency when properly performed and gauge pressure in psig on the gauge 44.

It will also be noted that there is a clear difference between the two temperature ranges and therefore the temperature of the pulp should be standardized between the various tests in order to have more meanful results. Freeness and pulping technique do not significantly effect the results obtained when applying the present invention.

Tests were also carried out on chemical pulps to determine the effectiveness and it was found that a similar relationship between consistency and pressure exists although the equipment may require calibration for the different pulps to be tested, i.e. the chemical pulps may require different pressure for equivalent consistency when compared with mechanical pulps. Table I indicates the results obtained with hardwood kraft.

TABLE I

| Consistency % Moisture Free | Pressure psig |
|---|---|
| 20 | 18 |
| 25 | 33 |
| 30 | 58 |
| 30.1 | 60 |
| 32.2 | 80 |
| 34.3 | 112 |
| 34.3 | 115 |
| 34.3 | 120 |
| 38.2 | 135 |
| 38.2 | 125 |
| 41.6 | 187 |
| 42.7 | 245 |

Modifications may be made without departing from the spirit of the invention as defined in the appended Claims.

We claim:

1. An apparatus for determining the consistency of a pulp having a consistency of between a 15 and 55% comprising; a container, a foraminous support means in the bottom of said container adapted to support a pulp sample and permit water from said pulp sample to pass therethrough, a water outlet from said container for water squeezed through said foraminous support means, pressure means for pressing a pulp sample in said container against said foraminous support and squeezing water from said pulp sample, and means for registering the pressure applied to said pulp sample at the initiation of flow of water through said outlet.

2. An apparatus as defined in claim 1 wherein said container is provided with means for heating same to hold the temperature of said pulp sample near a preselected temperature of between 20° C.–99° C.

3. An apparatus as defined in claim 1 wherein said means for applying pressure comprises a piston pressing on top of said pulp sample and means for moving said piston.

4. An apparatus as defined in claim 3 further comprising means for automatically determining the initiation of the flow of water through said outlet and registering said pressure.

5. A method for determining the consistency of a pulp comprising placing sample of said mechanical pulp having a consistency of between 15 and 55% into a container, supporting said sample of pulp on a foraminous support means gradually increasing the pressure applied to said pulp until water is squeezed therefrom and through said support, registering the pressure required to initiate flow of water through said foraminous support thereby to obtain indication of the consistency of said pulp sample.

6. A method as defined in claim 5 wherein the size of said sample pulp is randomly selected but is sufficient to maintain a mat on said foraminous support and at least 35 gms.

7. A method as defined in claim 5 further comprising maintaining the temperature of said pulp sample at a pre-selected value, between 20° C. and 99° C. while it is being pressed.

8. A method as defined in claims 5, 6 or 7 when said pressure is increased at a substantially constant rate of between 1 and 40 psi per second.

* * * * *